Figure 1:
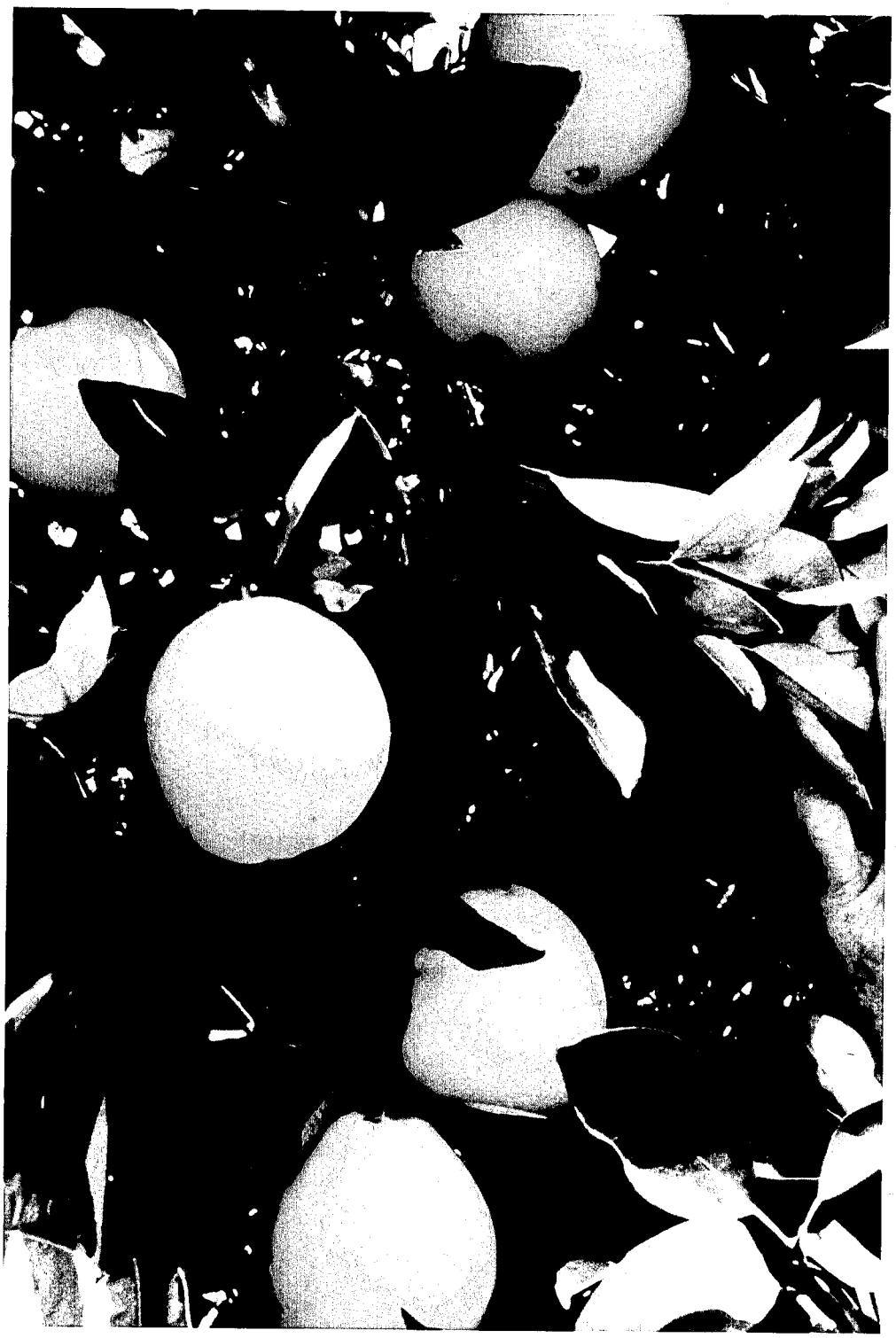

United States Patent [19]

Barnfield

[11] Patent Number: Plant 7,342

[45] Date of Patent: Oct. 2, 1990

[54] DISTINCT VARIETY OF ORANGE NAMED BARNFIELD LATE NAVEL

[75] Inventor: Wayne M. Barnfield, via Wentworth, Australia

[73] Assignee: Delwyn Barnfield, Ellerslie via Wentworth, Australia

[21] Appl. No.: 281,799

[22] Filed: Dec. 7, 1988

[30] Foreign Application Priority Data

Dec. 7, 1987 [AU] Australia ..... 82169/87

[51] Int. Cl.[5] ..... A01H 5/00

[52] U.S. Cl. ..... Plt./45

[58] Field of Search ..... Plt./45

*Primary Examiner*—Robert E. Bagwill

*Attorney, Agent, or Firm*—Lorance L. Greenlee

[57] ABSTRACT

A new cultiver of Naval Orange plant is characterized by its very late maturation and very late hanging.

3 Drawing Sheets

The present invention comprises a new and distinct variety of orange tree known by the name "Barnfield Late Navel".

The new variety was discovered growing among trees of the parent variety in an orchard in Ellerslie via Wentworth, New South Wales, Australia.

The parent is the well known "Washington Navel" variety.

The new variety was asexually reproduced at Ellerslie via Wentworth, New South Wales, Australia, by the present inventors. Horticultural examination of a subsequent of propagation has clearly demonstrated the combination of characteristics as herein disclosed for Barnfield Late Navel are firmly fixed and are retained through successive generations of asexual reproduction.

Barnfield Late Navel has not been observed under all possible environmental conditions. The prototype may vary significantly with variations in environment such as soil type and climate.

The following observations, measurements and comparisons described plants grown in Ellerslie via Wentworth, New South Wales, Australia.

The following traits have been repeatedly observed and are determined to be basic characteristics of Barnfield Late Navel, which in combination distinguish Barnfield Late Navel as a new and distinct variety.

(1) A very charasteristic late maturation.

(2) Very late hanging of fruit with the fruit retaining excellent internal and external condition.

(3) Naval orange characteristics such as seedlessness.

The following is a description of the Late Barnfield orange.

THE PLANT

Tree: Growing on *Poncirus trifoliata* rootstock. Medium vigor, dense, spreading.

Leaves: Medium large (80 to 100 mm×35 to 50 mm), variable, lanceolate to elliptical; apex variable, mainly acute but varying from acuminate to obtuse; base narrowed; edges entire to obsecurely crenate, marginal oil cells few; venation distinct; petioles winged; mature leaves dull, dark on upper surface, pale to light green on lower surface; texture crumpled to smooth.

Fruit: Large, globose to slightly oblong; base smooth, rounded; apex slightly depressed, sometimes slightly furrowed and broadly nippled with a normally open naval varying from small to large size; occasional seed; average diameter 7.5–9.5 cm; average weight ranges from 220 g in October to 356 g in January rind smooth to grained, medium thickness (average 5.2 mm); rind color changes from orange to deep orange up to December, to pale yellow-orange, with tinges of green by April; rind oil cells medium, slightly depressed, colored; interior segments usually 9 to 11; segment membranes thick but tender; pulp vesicles large-medium, long; very juicy, evenly distributed in sections; flavor rich, with acid and sugar well blended.

Figure 2:
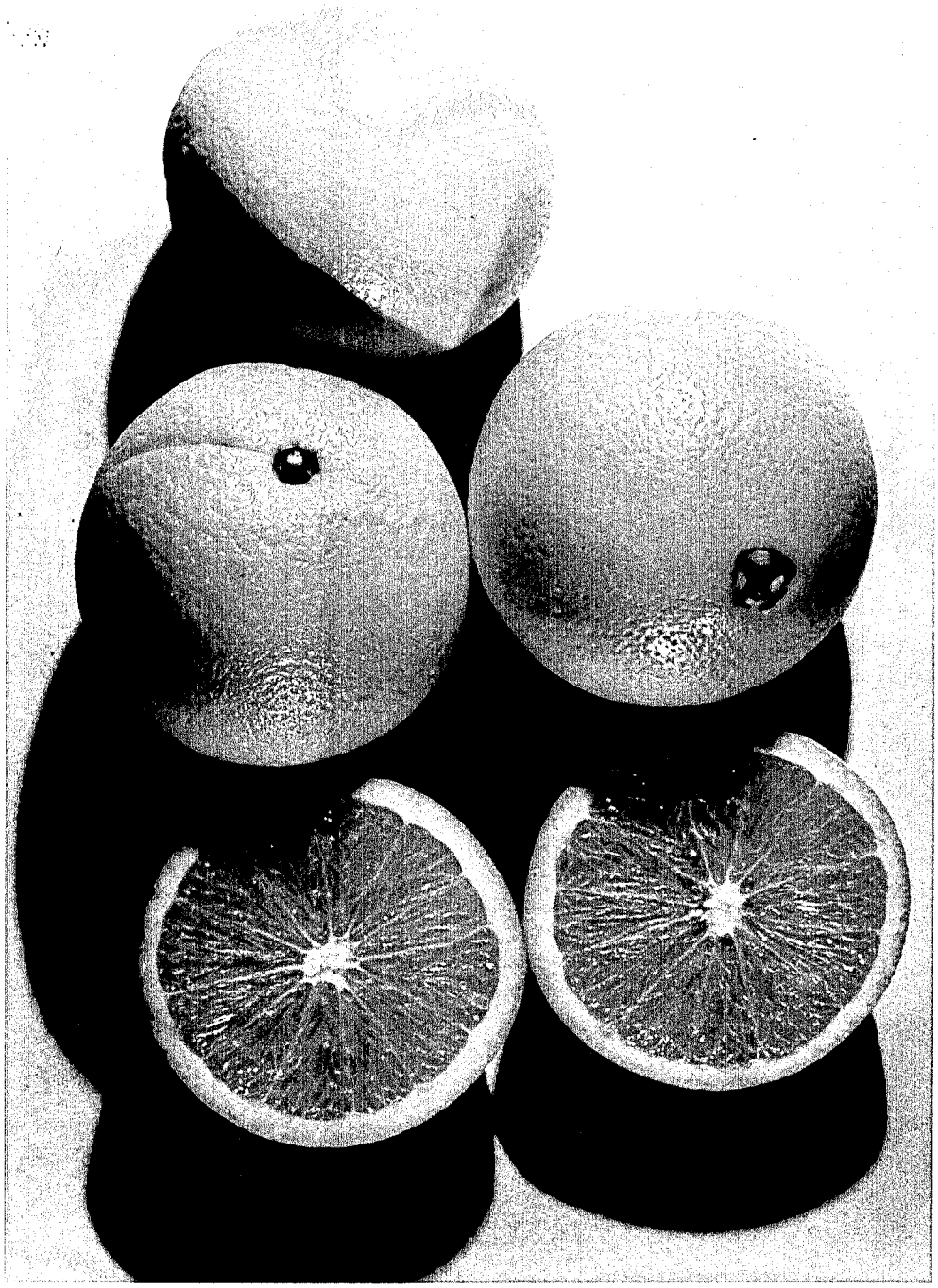
Figure 3:
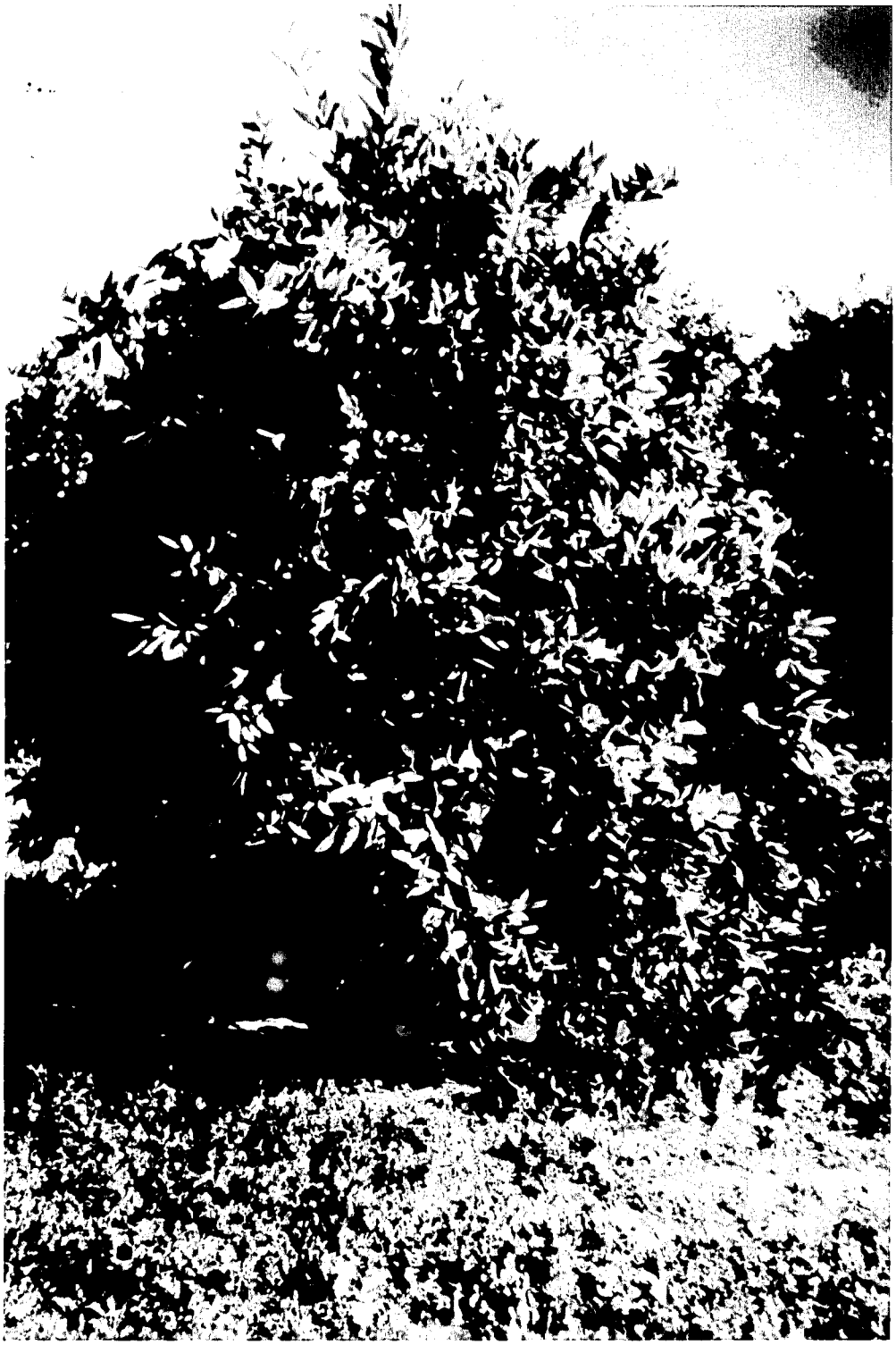

The accompanying photographic drawings illustrate characteristics of the Barnfield Late Navel tree and fruit FIG. 1 illustrates characteristics of the orange FIG. 2 shows details of the branches and leaves FIG. 3 shows an overall view of the tree.

Barnfield Late Navel can be compared with another Late Navel known as the Lane Late Navel, to date the navel with the latest hanging characteristics.

Flowering occurs at approximately the same time as the Lane Late Navel orange.

Fruit will hang on the tree in an excellent internal and external condition for approximately 150 days longer than the Lane Late Navel. The Lane Late Navel hangs rarely longer beyond November whereas the Barnfield Late Navel hang until April. Thereby filling in a gap in the season for Navel oranges.

The fruit maturity characteristics of the tree further characterize the tree (Table 1)

TABLE 1

Fruit quality comparison with the standard Lane Late Navel 10 fruits per sample

| | New Variety (28/4/87) | Lane (17/2/87) |
|---|---|---|
| Av. individual fruit wt. (g) | 332.5 | 264.9 |
| Fruit diameter (mm) | 90.4 | 79.0 |
| Rind thickness (mm) | 5.5 | 5.6 |
| Brix° | 10.7 | 13.0 |
| Acid (% citric) | 0.45 | 0.27 |
| Sugar:acid ratio | 27.3:1 | 48.1:1 |
| Juice (%) | 55.8 | 48.1 |
| Total soluble solids (kg/tonne) | 60.2 | 62.8 |

*The Lane Late Navel normally hangs on the tree in reasonable condition until December. The latest date of sampling possible for this variety before fruit drop occurred was 17/2/87.

I claim:

1. A new and distinct variety of Naval orange named Barnfield Late Navel, as illustrated and described, and particularly characterized by its late maturation, and very late hanging of fruit.

* * * * *